United States Patent
Baril et al.

(10) Patent No.: US 11,224,413 B2
(45) Date of Patent: Jan. 18, 2022

(54) RETRIEVAL DEVICE WITH BAG RELEASE MECHANISM

(71) Applicant: Covidien LP, Mansfield, MA (US)

(72) Inventors: Jacob C. Baril, Norwalk, CT (US); Saumya Banerjee, Hamden, CT (US); Brian Creston, Madison, CT (US)

(73) Assignee: Covidien LP, Mansfield, MA (US)

( * ) Notice: Subject to any disclaimer, the term of this patent is extended or adjusted under 35 U.S.C. 154(b) by 94 days.

(21) Appl. No.: 16/795,332

(22) Filed: Feb. 19, 2020

(65) Prior Publication Data
US 2021/0251620 A1 Aug. 19, 2021

(51) Int. Cl.
*A61B 17/00* (2006.01)

(52) U.S. Cl.
CPC .............. *A61B 17/00234* (2013.01); *A61B 2017/0042* (2013.01); *A61B 2017/00287* (2013.01); *A61B 2017/00336* (2013.01)

(58) Field of Classification Search
CPC ............ A61B 17/32056; A61B 17/221; A61B 17/0469; A61B 17/00234; A61B 2017/2212; A61B 2017/00269; A61B 2017/00867; A61B 2017/00353; A61B 2017/00358; A61B 2018/1407; A61B 2018/141; A61B 18/1492
See application file for complete search history.

(56) References Cited

U.S. PATENT DOCUMENTS

| | | | |
|---|---|---|---|
| 5,465,731 A * | 11/1995 | Bell | A61B 17/00234 600/562 |
| 5,971,995 A * | 10/1999 | Rousseau | A61B 17/00234 606/110 |
| 6,059,793 A | 5/2000 | Pagedas | |
| 6,156,055 A | 12/2000 | Ravenscroft | |
| 6,162,209 A | 12/2000 | Gobron et al. | |
| 6,171,317 B1 | 1/2001 | Jackson et al. | |
| 6,206,889 B1 | 3/2001 | Bennardo | |
| 6,224,612 B1 | 5/2001 | Bates et al. | |
| 6,228,095 B1 | 5/2001 | Dennis | |
| 6,248,113 B1 | 6/2001 | Fina | |
| 6,258,102 B1 | 7/2001 | Pagedas | |
| 6,264,663 B1 | 7/2001 | Cano | |
| 6,270,505 B1 | 8/2001 | Yoshida et al. | |
| 6,280,451 B1 | 8/2001 | Bates et al. | |
| 6,344,026 B1 | 2/2002 | Burbank et al. | |
| 6,350,266 B1 | 2/2002 | White et al. | |

(Continued)

*Primary Examiner* — Mohamed G Gabr
(74) *Attorney, Agent, or Firm* — Carter, DeLuca & Farrell LLP

(57) ABSTRACT

A specimen retrieval device includes outer and inner shafts. An end effector is supported on a distal end of the inner shaft and includes first and second arms that are configured to support a specimen bag. The first and second arms are movable via actuation of a handle between a proximal position wherein the first and second arms are retracted and a distal positon wherein the first and second arms are deployed and the specimen bag is positioned for receiving tissue. A release tube is disposed within a collar defined in the specimen bag and is configured to releasably engage respective first and second arms to provide stability when supporting the specimen bag and facilitate disengagement of the first and second arms from within the collar upon retraction of the first and second arms.

20 Claims, 6 Drawing Sheets

(56) References Cited

U.S. PATENT DOCUMENTS

| | | |
|---|---|---|
| 6,350,267 B1 | 2/2002 | Stefanchik |
| 6,358,198 B1 | 3/2002 | Levin et al. |
| 6,368,328 B1 | 4/2002 | Chu et al. |
| 6,383,195 B1 | 5/2002 | Richard |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,447,523 B1 | 9/2002 | Middleman et al. |
| 6,530,923 B1 | 3/2003 | Dubrul et al. |
| 6,537,273 B1 | 3/2003 | Sosiak et al. |
| 6,752,822 B2 | 6/2004 | Jespersen |
| 6,805,699 B2 | 10/2004 | Shimm |
| 6,951,533 B2 | 10/2005 | Foley |
| 6,986,774 B2 | 1/2006 | Middleman et al. |
| 7,037,275 B1 | 5/2006 | Marshall et al. |
| 7,052,501 B2 | 5/2006 | McGuckin, Jr. |
| 7,087,062 B2 | 8/2006 | Dhindsa |
| 7,101,379 B2 | 9/2006 | Gregory, Jr. et al. |
| 7,101,380 B2 | 9/2006 | Khachin et al. |
| 7,112,172 B2 | 9/2006 | Orban, III et al. |
| 7,115,125 B2 | 10/2006 | Nakao et al. |
| 7,144,400 B2 | 12/2006 | Byrum et al. |
| 7,169,154 B1 | 1/2007 | Que et al. |
| 7,229,418 B2 | 6/2007 | Burbank et al. |
| 7,285,126 B2 | 10/2007 | Sepetka et al. |
| 7,316,692 B2 | 1/2008 | Huffmaster |
| 7,357,801 B2 | 4/2008 | Burbank et al. |
| 7,534,252 B2 | 5/2009 | Sepetka et al. |
| 7,547,310 B2 | 6/2009 | Whitfield |
| 7,615,013 B2 | 11/2009 | Clifford et al. |
| 7,618,437 B2 | 11/2009 | Nakao |
| 7,654,283 B2 | 2/2010 | Seto et al. |
| 7,670,346 B2 | 3/2010 | Whitfield |
| 7,678,118 B2 | 3/2010 | Bates et al. |
| 7,722,626 B2 | 5/2010 | Middleman et al. |
| 7,727,227 B2 | 6/2010 | Teague et al. |
| 7,731,722 B2 | 6/2010 | Lavelle et al. |
| 7,731,723 B2 | 6/2010 | Kear et al. |
| 7,762,959 B2 | 7/2010 | Bilsbury |
| 7,762,960 B2 | 7/2010 | Timberlake et al. |
| 7,875,038 B2 | 1/2011 | Que et al. |
| 7,892,242 B2 | 2/2011 | Goldstein |
| 7,914,540 B2 | 3/2011 | Schwartz et al. |
| 7,918,860 B2 | 4/2011 | Leslie et al. |
| 7,955,292 B2 | 6/2011 | Leroy et al. |
| 8,057,485 B2 | 11/2011 | Hollis et al. |
| 8,075,567 B2 | 12/2011 | Taylor et al. |
| 8,118,816 B2 | 2/2012 | Teague |
| 8,152,820 B2 | 4/2012 | Mohamed et al. |
| 8,172,772 B2 | 5/2012 | Zwolinsk et al. |
| 8,211,115 B2 | 7/2012 | Cheng et al. |
| 8,282,572 B2 | 10/2012 | Bilsbury |
| 8,337,510 B2 | 12/2012 | Rieber et al. |
| 8,348,827 B2 | 1/2013 | Zwolinski |
| 8,409,216 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,486,087 B2 | 7/2013 | Fleming |
| 8,512,351 B2 | 8/2013 | Teague |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,956,370 B2 | 2/2015 | Taylor et al. |
| 8,968,329 B2 | 3/2015 | Cabrera |
| 8,986,321 B2 | 3/2015 | Parihar et al. |
| 9,005,215 B2 | 4/2015 | Grover et al. |
| 9,017,328 B2 | 4/2015 | Bahney |
| 9,017,340 B2 | 4/2015 | Davis |
| 9,033,995 B2 | 5/2015 | Taylor et al. |
| 9,084,588 B2 | 7/2015 | Farascioni |
| 9,101,342 B2 | 8/2015 | Saleh |
| 9,113,848 B2 | 8/2015 | Fleming et al. |
| 9,113,849 B2 | 8/2015 | Davis |
| 9,308,008 B2 | 4/2016 | Duncan et al. |
| 9,364,201 B2 | 6/2016 | Orban, III |
| 9,364,202 B2 | 6/2016 | Menn et al. |
| 9,370,341 B2 | 6/2016 | Ceniccola et al. |
| 9,370,378 B2 | 6/2016 | O'Prey et al. |
| 9,375,224 B2 | 6/2016 | Jansen |
| 9,414,817 B2 | 8/2016 | Taylor et al. |
| 9,468,542 B2 | 10/2016 | Hurley et al. |
| 9,486,188 B2 | 11/2016 | Secrest et al. |
| 9,522,034 B2 | 12/2016 | Johnson et al. |
| 9,549,747 B2 | 1/2017 | Carlson |
| 9,579,115 B2 | 2/2017 | Kahle et al. |
| 9,592,067 B2 | 3/2017 | Hartoumbekis |
| 9,622,730 B2 | 4/2017 | Farascioni |
| 9,624,638 B2 | 4/2017 | Lebreton et al. |
| 9,629,618 B2 | 4/2017 | Davis et al. |
| 9,655,644 B2 | 5/2017 | Collins |
| 9,730,716 B2 | 8/2017 | Secrest et al. |
| 9,789,268 B2 | 10/2017 | Hart et al. |
| 9,808,228 B2 | 11/2017 | Kondrup et al. |
| 9,826,997 B2 | 11/2017 | Cherry et al. |
| 9,867,600 B2 | 1/2018 | Parihar et al. |
| 9,877,893 B2 | 1/2018 | Taylor et al. |
| 2009/0192510 A1* | 7/2009 | Bahney ............ A61B 17/221 606/45 |
| 2020/0337686 A1* | 10/2020 | Baril ............ A61B 17/00234 |

* cited by examiner

RETRIEVAL DEVICE WITH BAG RELEASE MECHANISM

TECHNICAL FIELD

This disclosure relates to surgical instruments, and more particularly, to specimen retrieval devices that support tissue collection bags.

BACKGROUND

Specimen retrieval devices are commonly used during surgical procedures to collect and remove tissue specimens from a patient. Typically, during a surgical procedure in which tissue is transected, e.g., a hysterectomy procedure, a specimen retrieval device including a tissue collection bag is positioned to receive the tissue specimen once the tissue is transected. In some procedures, a grasper may be used to transfer the transected tissue specimen into the bag. Alternately, the bag may be positioned in relation to the tissue specimen to allow the tissue specimen to fall into the bag.

SUMMARY

In accordance with aspects of the present disclosure, a specimen retrieval device includes an outer shaft having a stationary handle on a proximal end portion thereof and an inner shaft supported within the outer shaft and having a movable handle on a proximal end portion thereof, the movable handle positioned to move relative to the stationary handle. An end effector is supported on a distal end of the inner shaft and includes a first arm and a second arm, the first arm including a first distal portion, the second arm including a second distal portion. The first and second arms are configured to releasably support a specimen bag thereon. The first and second arms are movable within the outer shaft via actuation of the handle between a proximal position wherein the first and second arms are retracted within the outer shaft and a distal positon wherein the first and second arms are deployed from the outer shaft and the specimen bag is positioned for receiving tissue. A release tube is disposed within a collar defined in the specimen bag and is configured to releasably engage respective first and second distal end portions of the first and second arms to provide stability when supporting the specimen bag and facilitate disengagement of the first and second arms from within the collar upon retraction of the first and second arms into the outer shaft.

In aspects according to the present disclosure, the release tube includes a weld or seam configured to facilitate deployment and retraction thereof. In other aspects according to the present disclosure, the release tube retains the first and second distal end portions of the respective first and second arms in a friction-fit manner. In still other aspects according to the present disclosure, upon retraction of the first and second arms within the outer shaft, the first and second arms disengage from the release tube to facilitate release of the specimen bag.

In aspects according to the present disclosure, the release tube is made from plastic, metal, or ceramic. In other aspects according to the present disclosure, the release tube includes a bias to facilitate deployment or retraction of the first and second arms. In yet other aspects according to the present disclosure, the release tube is made from a material having a sufficient strength, thickness and length to support heavy tissue within the specimen bag.

In aspects according to the present disclosure, the release tube is variable to support different tissue loads within the specimen bag. The variability of the release tube may be any combination of material, length, thickness, size or ease of release of the first or second arms. In aspects according to the present disclosure, the release tube is color-coded to indicate any combination of material, length, thickness, size or ease of release of the first or second arms.

In aspects according to the present disclosure, upon retraction, the force of the specimen bag against a distal end of the outer shaft forces the first and second arms to disengage with the release tube.

In accordance with aspects of the present disclosure, an end effector for a tissue specimen retrieval device includes a first arm and a second arm, the first arm including a first distal portion, the second arm including a second distal portion. The first and second arms are configured to support a specimen bag on the distal portions of the first and second arms. The first and second arms are movable between a first position wherein the first and second arms are retracted and closed and a second positon wherein the first and second arms are deployed and opened to unfurl a specimen bag configured to contain tissue. A release tube is disposed within a collar defined in the specimen bag and is configured to releasably engage respective first and second distal portions of the first and second arms to provide stability when supporting the specimen bag and facilitate disengagement of the first and second arms from within the collar upon retraction of the first and second arms to the first position.

In aspects according to the present disclosure, the release tube includes a weld or seam configured to facilitate deployment and retraction thereof. In other aspects according to the present disclosure, the release tube retains the first and second distal end portions of the respective first and second arms in a friction-fit manner. In still other aspects according to the present disclosure, upon retraction of the first and second arms, the first and second arms disengage from the release tube to facilitate release of the specimen bag.

In aspects according to the present disclosure, the release tube is made from plastic, metal, or ceramic. In other aspects according to the present disclosure, the release tube includes a bias to facilitate deployment or retraction of the first and second arms. In yet other aspects according to the present disclosure, the release tube is made from a material having a sufficient strength, thickness and length to support heavy tissue within the specimen bag.

In aspects according to the present disclosure, the release tube is variable to support different tissue loads within the specimen bag. The variability of the release tube may be any combination of material, length, thickness, size or ease of release of the first or second arms. In aspects according to the present disclosure, the release tube is color coded to indicate any combination of material, length, thickness, size or ease of release of the first or second arms.

In aspects according to the present disclosure, upon retraction, the force of the specimen bag against a distal end of the outer shaft forces the first and second arms to disengage with the release tube.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
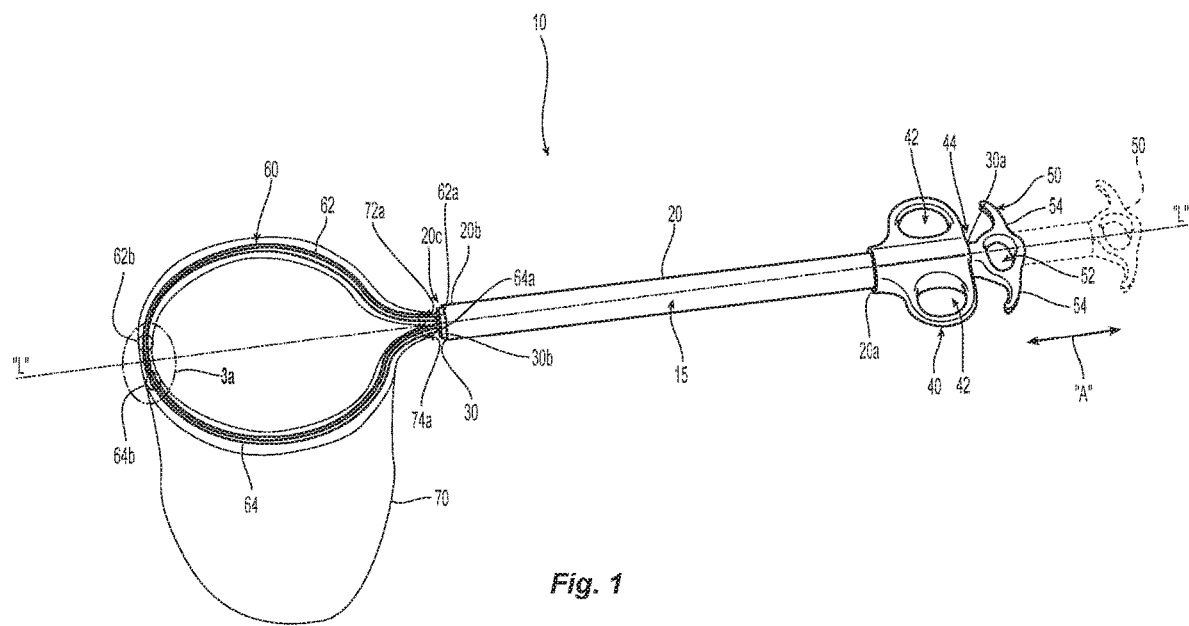
FIG. 1 is a perspective view of one embodiment of a specimen retrieval device in accordance with the principles of this disclosure, the specimen retrieval device illustrated in a position for collecting specimens with a release tube supporting a pair of arms of an end effector or flexible bag brim.

Embodiments of the disclosed specimen retrieval devices are described in detail with reference to the drawings, in which like reference numerals designate identical or corresponding elements in each of the several views. As commonly known, the term "clinician" refers to a doctor (e.g., a surgeon), a nurse, or any other care provider and may include support personnel. Additionally, the term "proximal" refers to the portion of structure that is closer to the clinician and the term "distal" refers to the portion of structure that is farther from the clinician. In the following description, well-known functions or constructions are not described in detail to avoid obscuring this disclosure in unnecessary detail.

In general, this disclosure describes a specimen retrieval device with bag release mechanisms to facilitate quick and easy removal of collection bags supported on the specimen retrieval device. In embodiments of this disclosure, a specimen retrieval device includes arms that are secured together by a release tube to create a single rigid ring for supporting a specimen bag and for providing leverage when loading a specimen in the specimen bag. The release tube enables the arms to separate so that the specimen bag can be removed from the specimen retrieval device, for instance, once a specimen is contained within the specimen bag.

With reference to FIGS. 1-4D, a specimen retrieval device 10 defines a longitudinal axis "L" and includes an elongated shaft assembly 15 having an outer shaft 20 and an inner shaft 30 supported within outer shaft 20. Outer shaft 20 has a proximal end portion 20a that supports a stationary handle 40 and a distal end portion 20b that defines a distal opening 20c. Stationary handle 40 defines finger openings 42 therethrough to facilitate grasping of stationary handle 40 by a user's fingers. Stationary handle 40 further defines a central opening 44 axially therethrough that is configured to slidably receive inner shaft 30 therein. Inner shaft 30 has a proximal end portion 30a that supports a movable handle 50 and a distal end portion 30b that supports an end effector 60.

Movable handle 50 defines a finger opening 52 therethrough and includes wings 54 that extend from opposite sides of movable handle 50. Finger opening 52 and wings 54 are configured to receive a user's fingers to facilitate finger gripping. Movable handle 50 is positioned to move axially along longitudinal axis "L," and relative to stationary handle 40, between distal and proximal positions, as indicated by arrows "A."

Figure 3A:
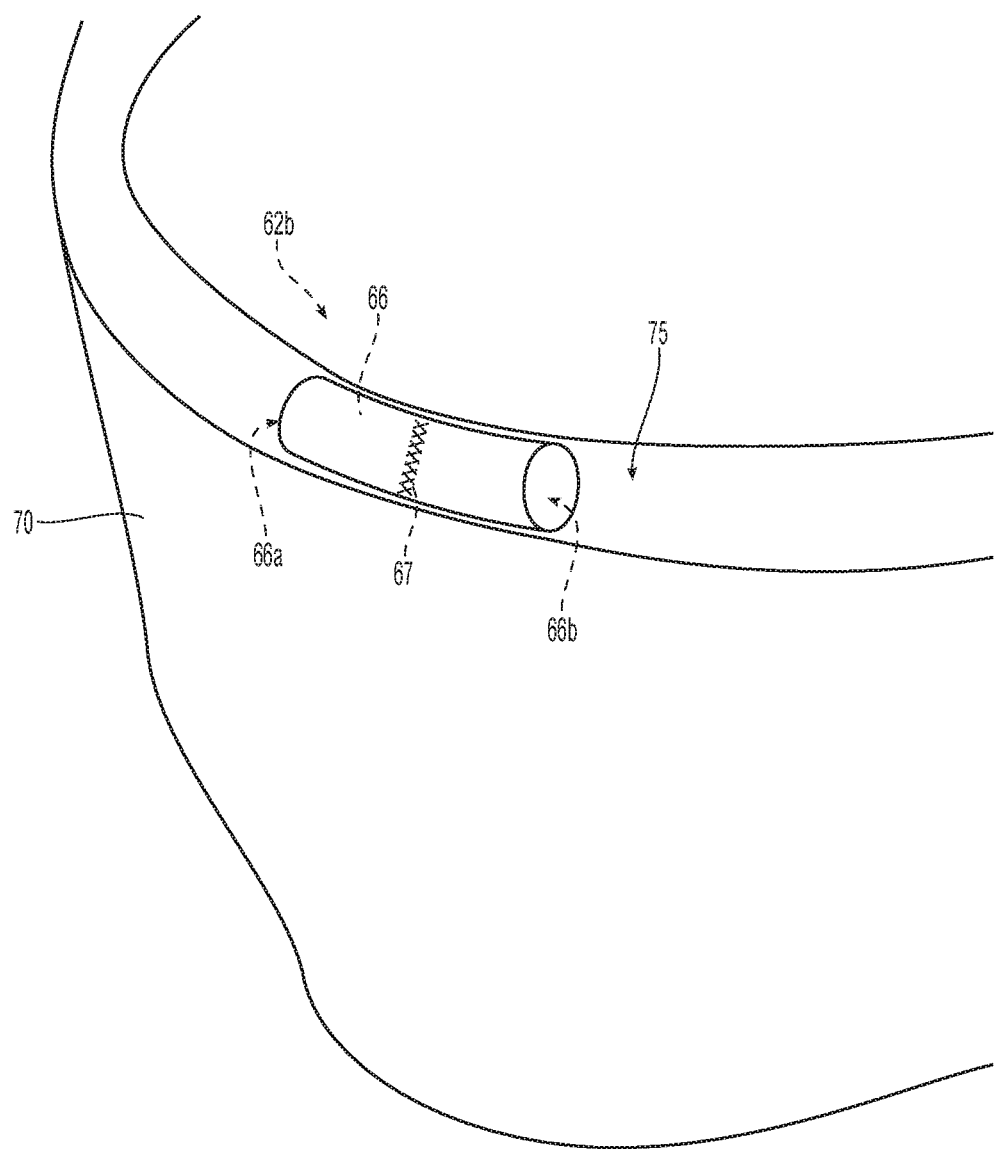
FIG. 3A is an enlarged, perspective view of the release tube disposed within a collar of the specimen bag.
Figure 3B:
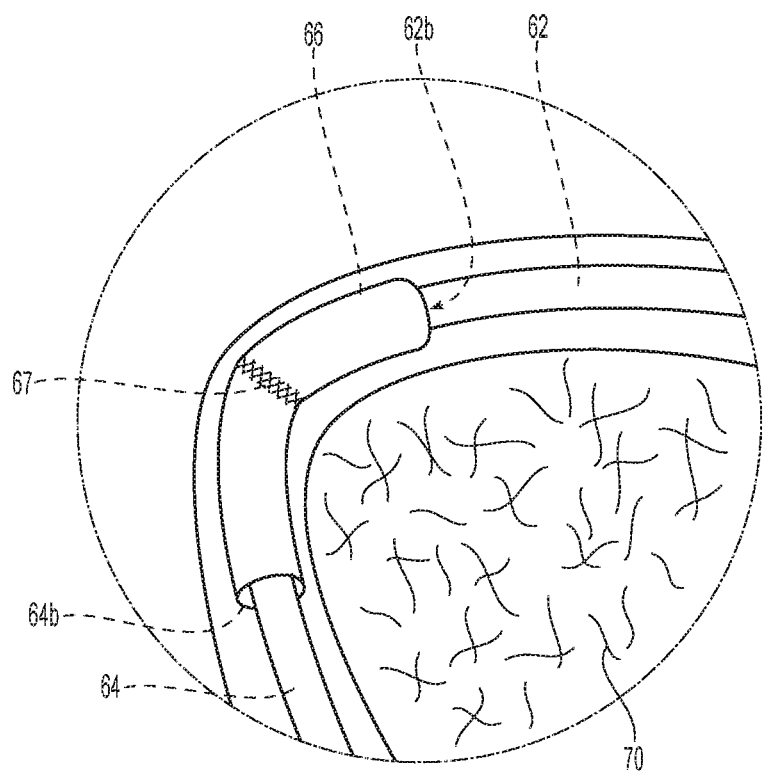
FIG. 3B is an enlarged, perspective view of the release tube disposed within the collar of the specimen bag with the pair of arms engaged within the release tube.

End effector or the flexible bag brim 60 of specimen retrieval device 10 supports a specimen bag 70 and includes a first arm 62 and a second arm 64 that define a ring when coupled together. First arm 62, which may have a hook or question mark shape, includes a proximal end portion 62a that curves distally to a distal end portion 62b. Second arm 64, which may also have a hook or question mark shape, includes a proximal end portion 64a that curves distally to a distal end portion 64b. First and second arms 62, 64 curve in opposite directions so as to be mirrored relative to one another about longitudinal axis "L." First and second distal end portions 62b, 64b are configured to generally abut one another as seen in FIG. 3B.

Release tube 66 includes openings 66a, 66b defined in either end thereof configured to receive the respective distal end portions 62b, 64b of the first and second arms 62, 64. Release tube 66 is dimensioned to frictionally reengage the respective arms 62, 64 and maintain the first and second arms 62, 64 in general alignment with one another and provide stability to the overall specimen retrieval device 10. Release tube 66 secures the distal portions 62b, 64b of the first and second arms 62, 64 together so that first and second arms 62, 64 form a unitary or single rigid ring that provides increased leverage against applied force when loading a specimen into specimen bag 70. Release tube 66 may be made from any substantially rigid plastic, metal, ceramic or other material that provides enough support to maintain the first and second arms 62, 64 in substantial alignment during tissue specimen "T" capture and retrieval (FIG. 4D).

Release tube 66 may include a bias to facilitate deployment or retraction of the first and second arms 62, 64. The length of the release tube 66 may be variable in strength, thickness, material and/or length to support different tissue loads. In other words, a first, preloaded release tube 66 may be used for a particular tissue load and another preloaded release tube 66 may be used to support a different, heavier load. A thicker release tube 66, a longer release tube 66, or a release tube 66 of a different material may be easier or harder to retract and/or crimp about a weld 67 as explained below. Or, the type of material or thickness of the release tube 66 may be varied to affect the ease of release of the first and second arms 62, 64. The release tubes 66 may be color coded for any of these purposes.

Figure 2:
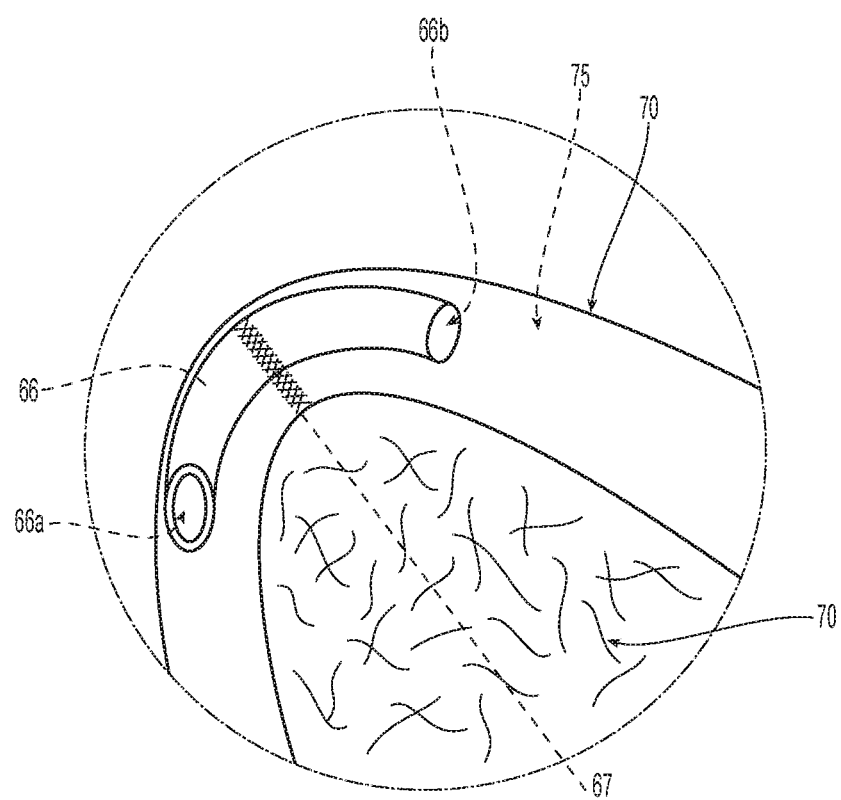
FIG. 2 is an enlarged, perspective view of the indicated area of detail shown in FIG. 1 shown with the pair of arms of the flexible bag brim engaged with the release tube within a collar of a specimen bag.

FIG. 2 shows the specimen bag 70 with the release tube 66 disposed with a collar 75 defined in specimen bag 70. Collar 75 is sized to receive the first and second arms 62, 64 and guide the first and second arms 62, 64 into a respective openings 66a, 66b of the release tube 66 (See FIG. 3B). Weld or seam 67 may be defined in the release tube 66 generally along a centerline thereof. Weld 67 allows the tube 66 to bend or crimp to facilitate deployment and retraction of the first and second arms 62, 64 within outer shaft 20 as explained below.

As seen in FIGS. 1 and 2, collar 75 includes a first arm channel 72 that has an open proximal end and second arm channel 74 that has as open proximal end. First arm channel 72 slidably receives first arm 62 of end effector 60 and second arm channel 74 slidably receives second arm 64 of end effector 60. During assembly, the distal ends of the first and second arms 62, 64 are introduced into the respective channels 72, 74 and engaged with the release tube 66.

Figure 4A:
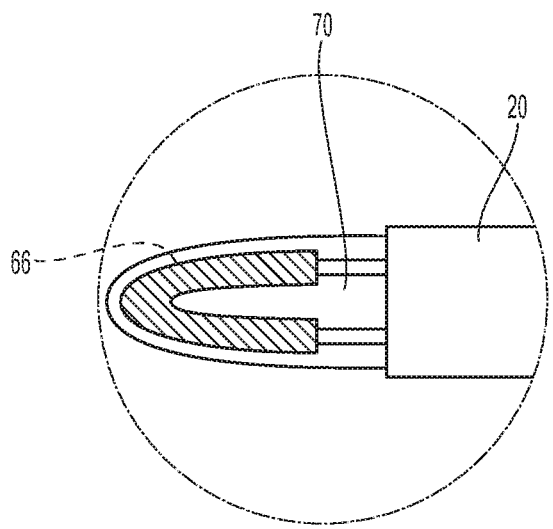
FIG. 4A is schematic view of the release tube and the specimen bag prior to deployment of the specimen bag.
Figure 4B:
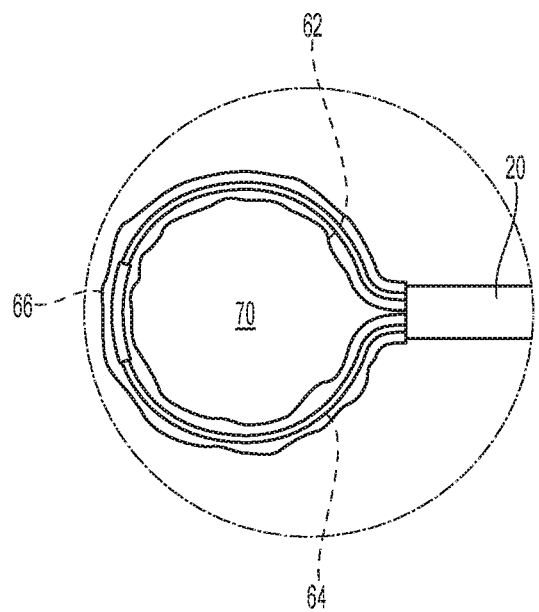
FIG. 4B is schematic view of the release tube and the specimen bag deployed for specimen collection.
Figure 4C:
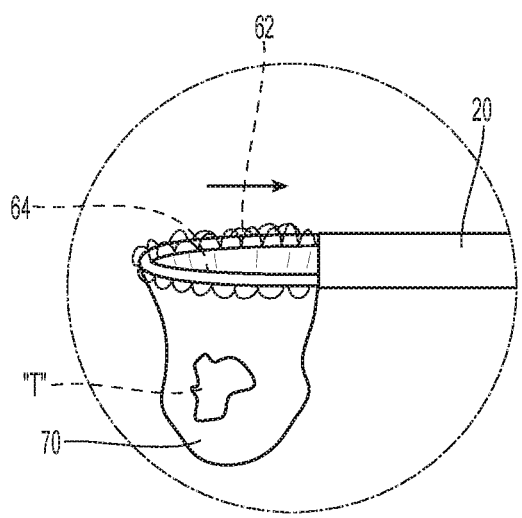
FIG. 4C is schematic view of the release tube and the specimen bag during retraction of the pair of arms of the flexible bag brim.
Figure 4D:
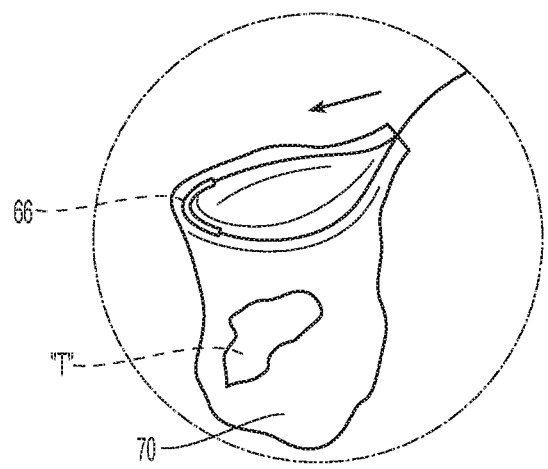
FIG. 4D is schematic view of the release tube and the specimen bag fully disengaged from the pair of arms of the flexible bag brim.

As illustrated in FIGS. 4A-4D, specimen retrieval device 10 can be provided in a retrieval configuration in which specimen bag 70 is mounted to first and second arms 62, 64 of end effector 60, release tube 66 is positioned to secure the distal ends 62b, 64b of first and second arms 62, 64, and movable handle 50 is disposed in a proximal position (FIG. 4A). The movable handle 50 is move to the distal position in contact with, or at least in close approximation to stationary handle 40, so that specimen retrieval device 10 is deployed and positioned for collecting a specimen (FIG. 4B). Once a specimen is collected in specimen bag 70 of specimen retrieval device 10, the movable handle 50 is pulled proximally causing release tube 66 to bend along weld 67 facilitating retraction of the first and second arms 62, 64 into outer shaft 20 and causing the first and second arms to disengage from release tube 66 under the force of retraction of the specimen bag against the outer shaft. Once the first and second arms 62, 64 are disengaged from release tube 66, the specimen bag 70 slips off the first and second arms 62, 64 during further retraction (FIG. 4C). Upon full retraction of the movable handle 50, the specimen bag 70 fully releases from the first and second arms 62, 64 (FIG. 4D).

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Pat. No. 8,828,023, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that this disclosure is not limited to the precise embodiments described, and that various other changes and modifications may be effected by one skilled in the art without departing from the scope or spirit of this disclosure. Additionally, the elements and features shown or described in connection with certain embodiments may be combined with the elements and features of certain other embodiments without departing from the scope of this disclosure, and that such modifications and variations are also included within the scope of this disclosure. Accordingly, the subject matter of this disclosure is not limited by what has been particularly shown and described.

The invention claimed is:

1. A specimen retrieval device, comprising:
   an outer shaft having a stationary handle on a proximal end portion thereof;
   an inner shaft supported within the outer shaft and having a movable handle on a proximal end portion thereof, the movable handle positioned to move relative to the stationary handle;
   an end effector supported on a distal end of the inner shaft and including a first arm and a second arm, the first arm including a first distal portion, the second arm including a second distal portion, the first and second arms configured to support a specimen bag on the first and second arms, the first and second arms movable within the outer shaft via actuation of the handle between a proximal position wherein the first and second arms are retracted within the outer shaft and a distal position wherein the first and second arms are deployed and the specimen bag is positioned for receiving tissue; and
   a release tube disposed within a collar defined in the specimen bag and configured to releasably engage respective first and second distal portions of the first and second arms to provide stability when supporting the specimen bag and facilitate disengagement of the first and second arms from within the collar upon retraction of the first and second arms into the outer shaft.

2. The specimen retrieval device of claim 1, wherein the release tube includes a weld or seam configured to facilitate deployment and retraction thereof.

3. The specimen retrieval device of claim 1, wherein the release tube retains the first and second distal portions of the respective first and second arms in a friction-fit manner.

4. The specimen retrieval device of claim 1, wherein upon retraction of the first and second arms within the outer shaft, the first and second arms disengage from the release tube to facilitate release of the specimen bag.

5. The specimen retrieval device of claim 1, wherein the release tube is made from plastic, metal, or ceramic.

6. The specimen retrieval device of claim 1, wherein the release tube includes a bias to facilitate deployment or retraction of the first and second arms.

7. The specimen retrieval device of claim 1, wherein the release tube is made from a material having a sufficient strength, thickness and length to support heavy tissue within the specimen bag.

8. The specimen retrieval device of claim 1, wherein the release tube is variable to support different tissue loads within the specimen bag.

9. The specimen retrieval device of claim 8, wherein the variability of the release tube includes any combination of material, length, thickness, size or ease of release of the first or second arms.

10. The specimen retrieval device of claim 8, wherein the release tube is color coded to indicate any combination of material, length, thickness, size or ease of release of the first or second arms.

11. The specimen retrieval device of claim 8, wherein upon retraction, the force of the specimen bag against a distal end of the outer shaft forces the first and second arms to disengage with the release tube.

12. An end effector for a tissue specimen retrieval device, comprising:
   a first arm and a second arm, the first arm including a first distal portion, the second arm including a second distal portion, the first and second arms configured to support a specimen bag on the first and second arms, the first and second arms movable between a first position wherein the first and second arms retracted and closed and a second position wherein the first and second arms are deployed and opened to unfurl a specimen bag configured to contain tissue; and
   a release tube disposed within a collar defined in the specimen bag and configured to releasably engage respective first and second distal portions of the first and second arms to provide stability when supporting the specimen bag and facilitate disengagement of the first and second arms from within the collar upon retraction of the first and second arms to the first position.

13. The specimen retrieval device of claim 12, wherein the release tube includes a weld or seam configured to facilitate deployment and retraction thereof.

14. The specimen retrieval device of claim 12, wherein the release tube retains the first and second distal portions of the respective first and second arms in a friction-fit manner.

15. The specimen retrieval device of claim 12, wherein upon retraction of the first and second arms, the first and second arms disengage from the release tube to facilitate release of the specimen bag.

16. The specimen retrieval device of claim 12, wherein the release tube is made from plastic, metal, or ceramic.

17. The specimen retrieval device of claim 12, wherein the release tube includes a bias to facilitate deployment or retraction of the first and second arms.

18. The specimen retrieval device of claim 12, wherein the release tube is made from a material having a sufficient strength, thickness and length to support heavy tissue within the specimen bag.

19. The specimen retrieval device of claim 12, wherein the release tube is variable to support different tissue loads within the specimen bag.

20. The specimen retrieval device of claim 19, wherein the variability of the release tube includes any combination of material, length, thickness, size or ease of release of the first or second arms.

* * * * *